United States Patent [19]
Krug et al.

[11] Patent Number: 5,559,254
[45] Date of Patent: Sep. 24, 1996

[54] SEPARATION OF A MIXTURE OF METHANOL AND TETRAHYDROFURAN INTO ITS CONSTITUENTS

[75] Inventors: Joseph Krug, Weisenheim am Berg; Christof Palm, Ludwigshafen, both of Germany

[73] Assignee: BASF Aktiengesellschaft, Ludwigshafen, Germany

[21] Appl. No.: 403,770

[22] PCT Filed: Nov. 12, 1993

[86] PCT No.: PCT/EP93/03184

§ 371 Date: Mar. 24, 1995

§ 102(e) Date: Mar. 24, 1995

[87] PCT Pub. No.: WO94/12456

PCT Pub. Date: Jun. 9, 1994

[30] Foreign Application Priority Data

Nov. 21, 1992 [DE] Germany ............... 42 39 243.8

[51] Int. Cl.$^6$ ............... C07D 307/06; C07D 307/08
[52] U.S. Cl. ............... 549/429; 549/509; 568/913; 568/918
[58] Field of Search ............... 549/429, 509; 568/913, 918

[56] References Cited

U.S. PATENT DOCUMENTS

| | | | |
|---|---|---|---|
| 4,798,674 | 1/1989 | Pasternak et al. | 210/640 |
| 5,207,909 | 5/1993 | Abeles | 210/500.27 |
| 5,248,427 | 9/1993 | Spiske et al. | 210/640 |
| 5,360,923 | 11/1994 | Nickel et al. | 558/277 |

FOREIGN PATENT DOCUMENTS

| | | |
|---|---|---|
| 022469 | 1/1981 | European Pat. Off. . |
| 423949 | 4/1991 | European Pat. Off. . |
| 476370 | 3/1992 | European Pat. Off. . |
| 2242429 | 10/1991 | United Kingdom . |

*Primary Examiner*—Ba Kim Trinh
*Attorney, Agent, or Firm*—Keil & Weinkauf

[57] ABSTRACT

A process is disclosed for separating a mixture of methanol and tetrahydrofuran into its components. The separation is carried out in the liquid or gaseous phase through an organophilic membrane, for example, a plasma polymerization membrane.

4 Claims, 2 Drawing Sheets

SEPARATION OF A MIXTURE OF METHANOL AND TETRAHYDROFURAN INTO ITS CONSTITUENTS

This is a 371 application of PCT/EP93/03184 dated Nov. 12, 1993.

The present invention relates to a process for separating a mixture of methanol and tetrahydrofuran into its constituents and to the separation of a methanol/water/tetrahydrofuran mixture into a methanol/water mixture and tetrahydrofuran.

Tetrahydrofuran (THF) is frequently used as solvent, reaction medium and starting material for various syntheses in the chemical industry, for example for preparing adhesives, special paints, coatings, fibers, in the extraction of specific active substances, for recrystallization of certain compounds or as starting material for various syntheses in a number of reactions. After these uses, the THF is often contaminated with methanol or methanol and water.

Since an azeotropic mixture cannot be completely broken down into its components in just one column with stationary operation, simple rectification, for example, of this mixture is possible only as far the azeotrope. The methanol/THF azeotrope contains 31% by weight methanol and boils at 60.7° C. under atmospheric pressure (minimum azeotrope), the water/THF azeotrope contains 5.3% by weight water and boils at 64° C. under atmospheric pressure, and the methanol/water/THF mixture forms two binary minimum azeotropes under atmospheric pressure and is divided by the distillation line between these azeotropes into regions I and II, see FIG. 1. In order, for example, to obtain THF from region I it is therefore necessary to cross the distillation line. It is generally known in respect of ternary mixtures that only one pure substance (not that with the intermediate boiling point) can be obtained in a single rectification step. If the individual components form azeotropes, the situation becomes complicated. This is why special distillation processes are frequently employed in industry to overcome this distillation limit either by utilizing properties intrinsic to the system, such as by changing the pressure or by adding an auxiliary such as an entrainer, see Ullmanns Encyklopädie der technischen Chemie, 4th edition, volume 2, pages 489–545.

However, all these special processes are elaborate because they require at least two or three and frequently even more columns and other equipment such as pressure elevation stages, decanters etc., and the associated connections, return lines, auxiliary workup systems (with losses thereof) etc.

EP-A 22 469 describes a process for removing methanol from mixtures of tetrahydrofuran with methanol and water. This entails at least two columns which are operated under different pressures being coupled together so that the top product of the column under the higher pressure is rich in methanol, while the bottom product of this colunm is water- and methanol-free tetrahydrofuran (page 2, line 26 to page 3, line 15).

It is an object of the present invention
a) on the one hand to separate a mixture of methanol and THF into its constituents and
b) on the other hand to separate a methanol/water/THF mixture into a methanol/water mixture and THF and
c) at the same time in each case to purify THF to levels ≧99.9% by weight simply and without great losses.

We have found that this object is achieved by carrying out the separations by pervaporation, with the separations taking place in the liquid or gas phase by means of an organophilic/hydrophilic membrane, for example a plasma polymerization membrane.

Further features of the process according to the invention are defined in the independent claims.

These are, on the one hand, the separation of mixtures composed of methanol or methanol/water and aliphatic and/or aromatic ethers of the formula I

$$R^1\text{—}O\text{—}R^2 \qquad (I)$$

where $R^1$ and $R^2$ are identical or different and are each linear or branched $C_1$-$C_6$-alkyl,
$C_2$-$C_6$-alkenyl,
$C_6$-$C_{12}$-aryl,
it being possible for these groups to be substituted by hydroxyl and/or alkoxy groups with 1–4 carbons, wherein the separation is carried out by pervaporation using an organophilic/hydrophilic membrane, and, on the other hand, the separation of mixtures composed of methanol and cyclic ethers of the formula II or methanol/water and cyclic ethers of the formula II

(II)

where $R^3$ is
$C_4$-$C_6$-alkylene which can be substituted by
$C_1$-$C_4$-alkyl groups, or is
$C_2$-$C_8$-alkylene which can be interrupted 1 to 4 times by oxygen atoms and can be substituted by $C_1$-$C_4$-alkyl groups, wherein the separation is carried by pervaporation using an organophilic/hydrophilic membrane.

The process can be carried out industrially either batchwise or continuously.

EXAMPLE 1

Batchwise process—removal of methanol from THF by pervaporation

Figure 1:
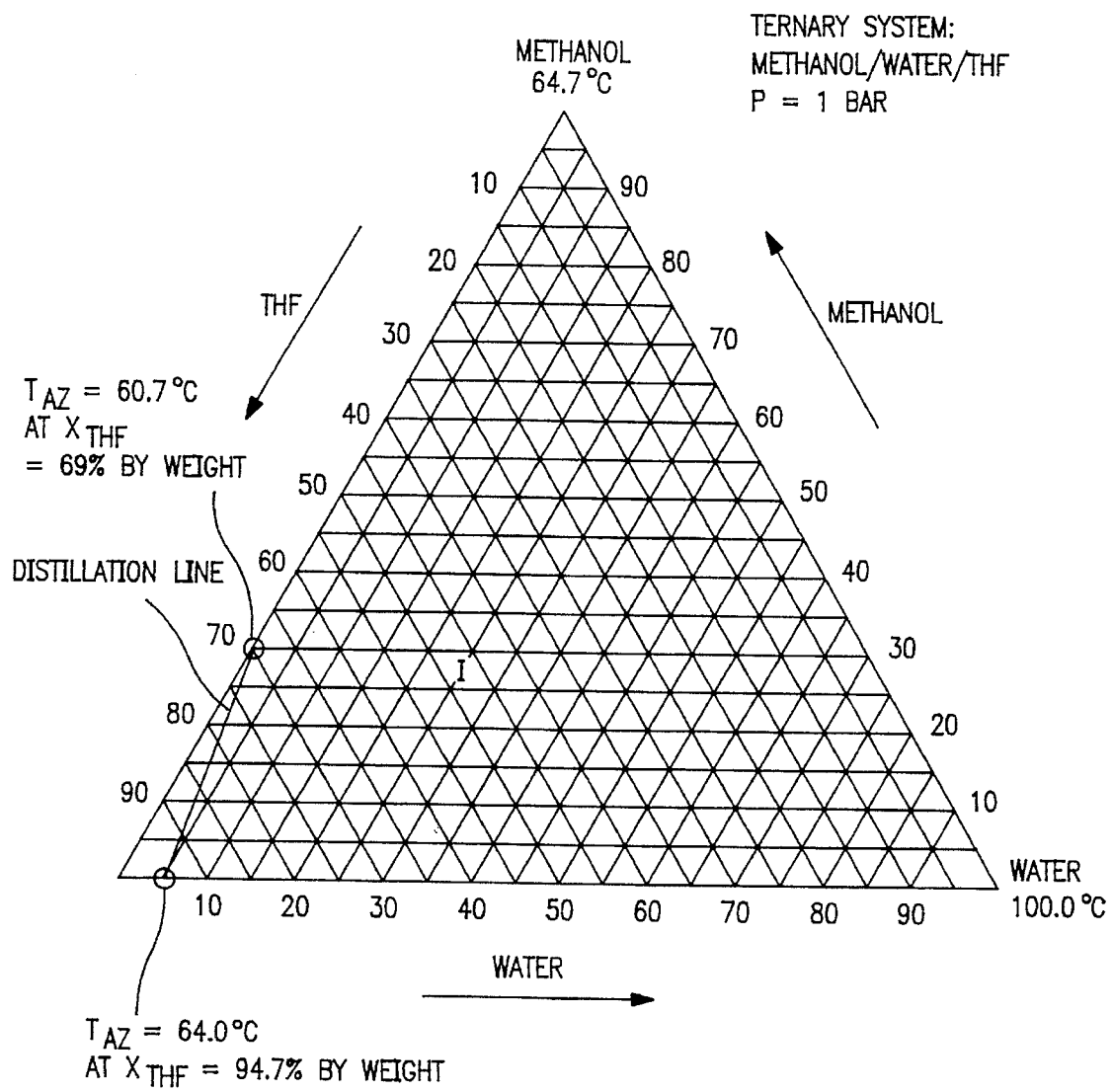
FIG. 1 is a ternary diagram of methanol/water/THF.
Figure 2:
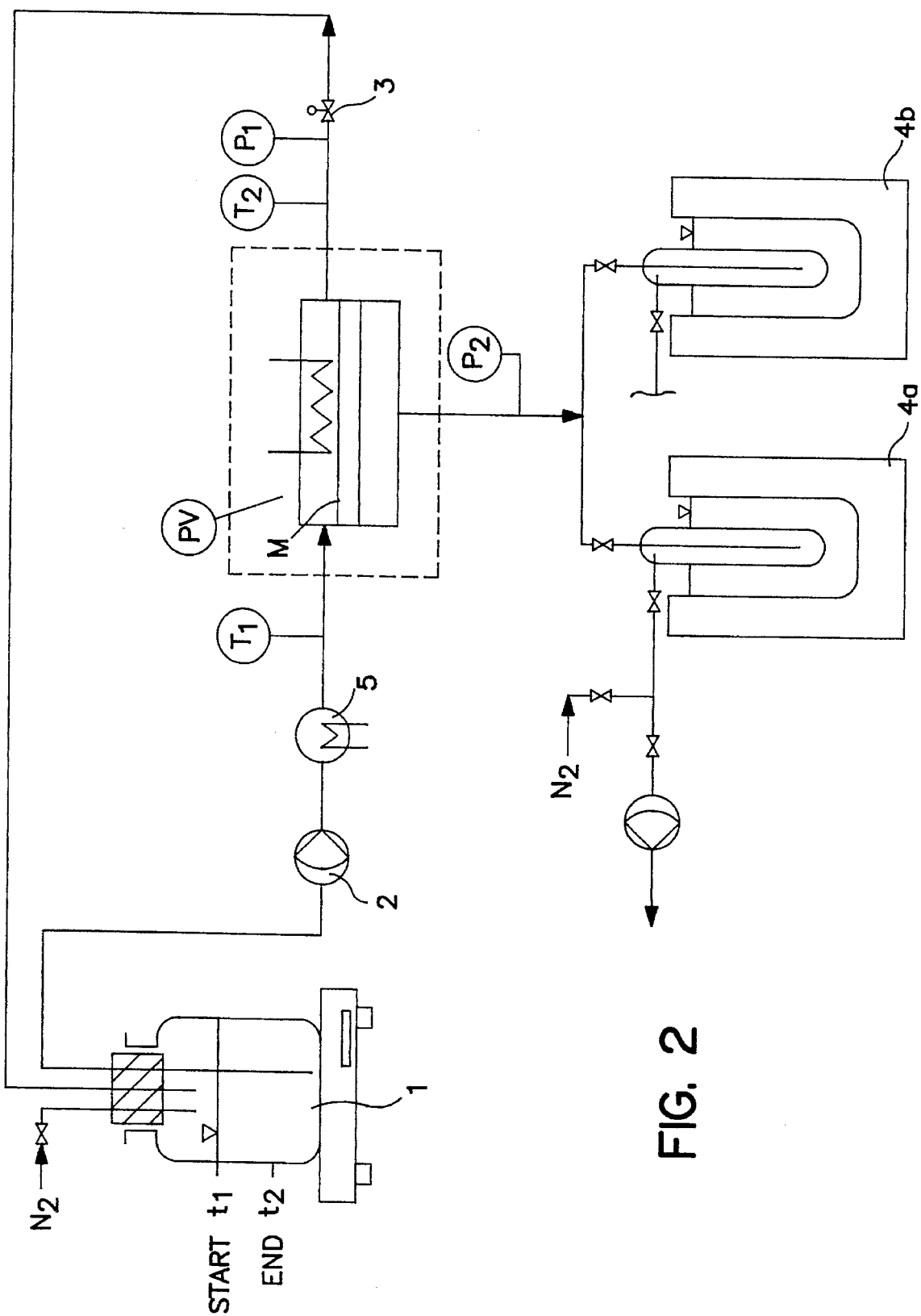
FIG. 2 depicts a batchwise process for removing methanol or methanol and water from THF by pervaporation.

The batchwise process is depicted in FIG. 2. In this case, 824 g of a mixture of 85.0% by weight THF and 15.0% by weight methanol is introduced into container 1 at room temperature and circulated through pump 2 and the test cell PV with a membrane area M of 100 cm² about 7 times an hour. A gage pressure of 3.5 bar is set at the pressure-maintenance valve 3. The absolute pressure on the permeate side is 15 mbar. The permeate is frozen out at about −80° C. in cold traps 4a and 4b. The permeate and retentate are initially analyzed about every 7 to 24 hours. The composition in the feed is determined as a function of the time. After the startup procedure with a feed temperature of 50° C. for 54 hours, the feed is heated from room temperature of about 20° C. to 80° C. in the course of one hour, and kept constant, by thermostat 5 (time t1). The difference between the feed temperature T1 (PV in) and the retentate temperature T2 (PV out) is then about 0.8° C. at time t1 and <0.1° C. at time t2. After 263 hours (time t2), the amount of final product is 689 g containing 99.9% by weight THF and about 0.1% by weight methanol. 135 g containing 8.9% by weight THF and 91.1% by weight methanol have permeated through the plasma polymerization membrane. The total flux has decreased during this from about 0.2 kg/m²h to 0.02 kg/m²h.

EXAMPLE 2

Batchwise process—removal of methanol and water from THF by pervaporation

The batchwise process is depicted in FIG. 2. In this case, 944 g of a mixture of 69.6% by weight THF, 20.8% by weight methanol and 9.6% by weight water is introduced into container 1 at room temperature and circulated through pump 2 and test cell PV with a membrane area M of 100 cm² about 7 times an hour. A gage pressure of 3.5 bar is set at the pressure-maintenance valve 3. The absolute pressure on the permeate side is 15 mbar. The permeate is frozen out at about −70° C. in cold traps 4a and 4b. The permeate and retentate are analyzed on average every hour in the first 6 hours and then about every 16 hours. The composition of the feed is determined as a function of the time, for which purpose a total of about 143 g of THF, 17 g of methanol and about 2 g of water are removed. After the startup procedure, the feed is heated from room temperature of about 20° C. to 80° C. in the course of one hour, and kept constant, by thermostat 5 (time t1). The difference between the feed temperature T1 (PV in) and the retentate temperature T2 (PV out) is then about 5° C. at time t1 and <0.1° C. at time t2. After 167 hours (time t2), the amount of final product is 539 g containing >99% by weight THF, <0.8% by weight methanol and about 1000 ppm water. 293 g containing 5.1% by weight THF, 63.5% by weight methanol and 31.4% by weight water have permeated through the plasma polymerization membrane. The total flux has decreased during this from 3.1 kg/m²h to about 0.01 kg/m²h.

The advantages of the invention are that the process is simpler and thus more economic for removing methanol or methanol and water from THF via the azeotrope or via the distillation line in the ternary diagram by means of pervaporation to purities of about 99.9% by weight THF.

We claim:

1. A process for separating a mixture of methanol and tetrahydrofuran into its constituents in a liquid or gas phase, wherein the separation is carried out by pervaporation using as an organophilic/hydrophilic membrane, a plasma polymerization membrane.

2. A process for separating a mixture of methanol/water/tetrahydrofuran mixture in to a methanol/water mixture and tetrahydrofuran in a liquid or gas phase, wherein the separation is carried out by pervaporation using as an organophilic/hydrophilic membrane, a plasma polymerization membrane.

3. A process for separating mixtures composed of methanol or methanol/water and aliphatic and/or aromatic ethers of the formula I $$R^1 \text{---} O \text{---} R^2 \qquad (I)$$

where $R^1$ and $R^2$ are identical or different and are each linear or branched $C_1$-$C_6$-alkenyl, $C_2$-$C_6$-alkenyl, $C_6$-$C_{12}$-aryl, it being possible for these groups to be substituted by hydroxyl and/or alkoxy groups with 1–4 carbons wherein the separation is carried out in a liquid or gas phase by pervaporation using as an organophilic/hydrophilic membrane, a plasma polymerization membrane.

4. A process for separating mixtures composed of methanol and cyclic ethers of the formula II, or methanol/water and cyclic ethers of the formula II

where $R^3$ is $C_4$-$C_6$-alkylene which can be substituted by $C_1$-$C_4$-alkyl groups, or is $C_2$-$C_8$-alkylene which can be interrupted 1 to 4 times by oxygen atoms and can be substituted by $C_1$-$C_4$-alkyl groups in a liquid or gas phase, wherein the separation is carried out by pervaporation using as an organophilic/hydrophilic membrane, a plasma polymerization membrane.

\* \* \* \* \*